(12) United States Patent
Ballard et al.

(10) Patent No.: US 6,279,743 B1
(45) Date of Patent: Aug. 28, 2001

(54) DEVICE FOR FACILITATING ENGAGEMENT AND DISENGAGEMENT BETWEEN NEEDLES AND ASSOCIATED SYRINGES AND SHEATHS AND FOR RECEIVING SHARPS

(75) Inventors: Jerome D. Ballard; Carol H. Ballard, both of Tega Cay; Timothy D. Giles, Rock Hill, all of SC (US)

(73) Assignee: Cambridge Marketing, Inc., Rock Hill, SC (US)

( * ) Notice: Subject to any disclaimer, the term of this patent is extended or adjusted under 35 U.S.C. 154(b) by 0 days.

(21) Appl. No.: 09/546,587

(22) Filed: Apr. 11, 2000

(51) Int. Cl.[7] ............................. B65A 83/10; A61B 19/10
(52) U.S. Cl. ..................... 206/364; 128/852; 206/365; 206/366; 211/70.6; 604/356
(58) Field of Search ................... 206/363–365, 206/366, 370; 211/70.6; 604/192, 356; 128/849–856

(56) References Cited

U.S. PATENT DOCUMENTS

| | | |
|---|---|---|
| 4,570,628 * | 2/1986 | Neal ...................................... 128/853 |
| 4,973,315 | 11/1990 | Sincock . |
| 5,005,590 * | 4/1991 | Eldridge, Jr. et al. ................ 128/849 |
| 5,097,963 * | 3/1992 | Chernosky et al. .............. 206/366 X |
| 5,183,469 * | 2/1993 | Capaccio ........................... 206/365 X |
| 5,195,538 * | 3/1993 | Eldridge, Jr. et al. ................ 128/849 |
| 5,265,724 | 11/1993 | Dondlinger . |
| 5,279,578 * | 1/1994 | Cooke .............................. 206/365 X |
| 5,334,151 | 8/1994 | Santilli . |
| 5,469,964 * | 11/1995 | Bailey ............................. 206/370 X |
| 5,607,403 | 3/1997 | Kretzschmar et al. . |
| 5,799,788 | 9/1998 | Web . |
| 5,868,250 * | 2/1999 | Brackett ............................... 206/363 |
| 5,975,295 | 11/1999 | Diamond . |

* cited by examiner

*Primary Examiner*—Bryon P. Gehman
(74) *Attorney, Agent, or Firm*—Alston & Bird LLP

(57) ABSTRACT

A device for manipulation of a syringe needle and for sharps disposal is provided. Beneficially, in one aspect, single-handed use of the device is facilitated. In another aspect, the device includes advantageous features for guiding a needle tip into a needle cap. In yet other aspects, the device beneficially includes a protective cover which prevents accidental loss of used sharps from the device, and the device includes an aperture which engages a needle cap by cutting into the needle cap.

20 Claims, 3 Drawing Sheets

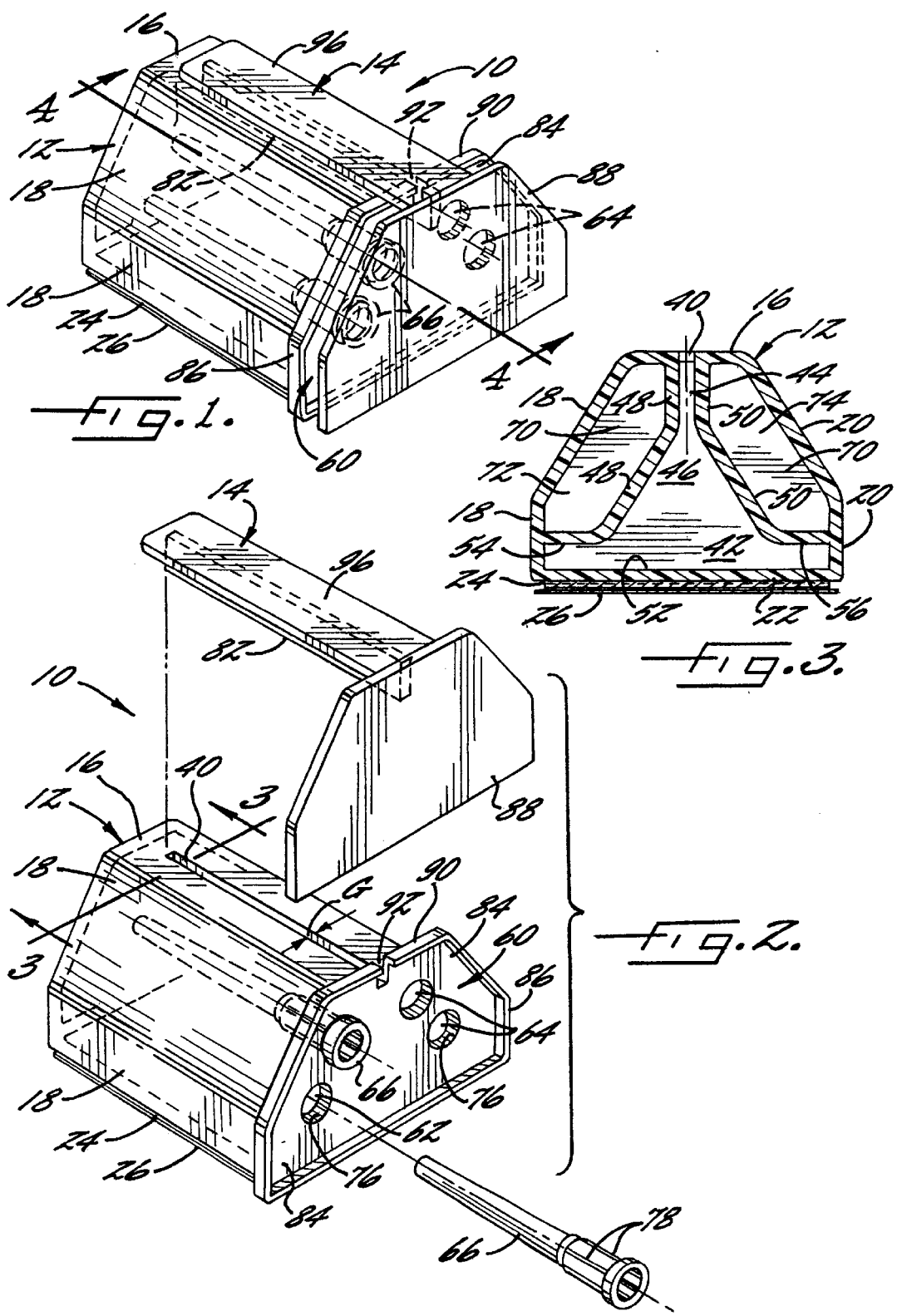

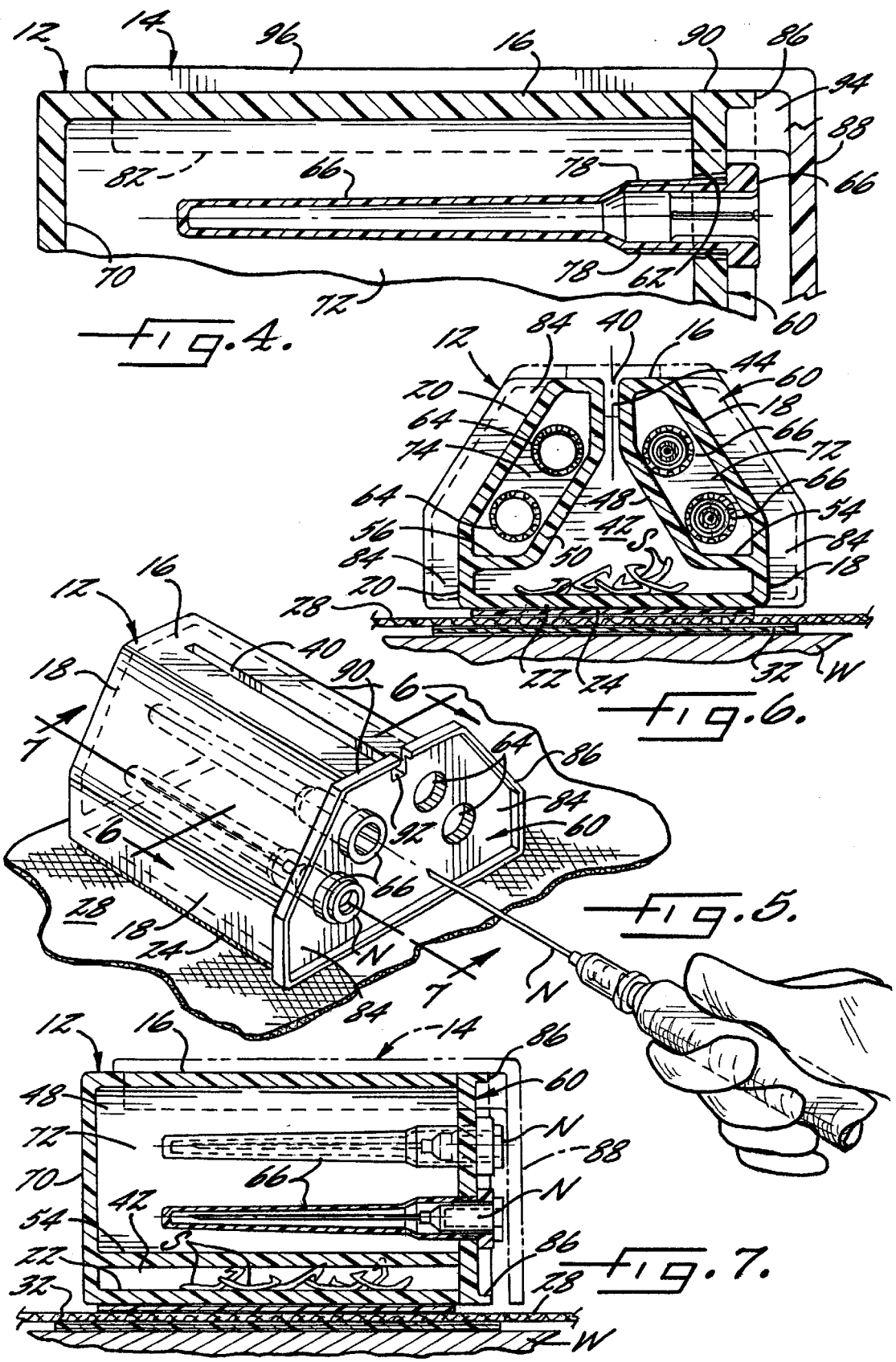

DEVICE FOR FACILITATING ENGAGEMENT AND DISENGAGEMENT BETWEEN NEEDLES AND ASSOCIATED SYRINGES AND SHEATHS AND FOR RECEIVING SHARPS

BACKGROUND OF THE INVENTION

This invention relates generally to the manipulation, storage and disposal of sharps.

As exemplified by U.S. Pat. No. 5,265,724 to Dondlinger and U.S. Pat. No. 5,975,295 to Diamond, apertures of varying sizes and configurations for frictionally engaging a needle cap when capping and uncapping a syringe needle, are known. To avoid accidental sticks, single-handed manipulation of syringe needles and other sharps is desirable. Thus, it is known, as illustrated by the Dondlinger patent and U.S. Pat. No. 5,334,151 to Santilli, U.S. Pat. No. 5,607,403 to Kretzschmar et al, and U.S. Pat. No. 5,799,788 to Webb, to provide a receptacle for sharps disposal or assisting in capping and uncapping syringe needles, with an adhesive surface for attaching the receptacle to a surface. Furthermore, it is known, as exemplified by the Kretzschmar et al patent and U.S. Pat. No. 4,973,315 to Sincock, to use a bull's-eye ring or radially extending cap flange to guide a needle tip into a needle cap. Moreover, it is known as illustrated by the Dondlinger patent, to protectively cover a sharps disposal receptacle after use.

However, it would be advantageous if a device for manipulation of a syringe needle and for sharps disposal, were immovably fixed on a sterile field during use. Furthermore, an improved device for manipulation and containment of syringe needles and other sharps, is needed.

SUMMARY OF THE INVENTION

In accordance with one aspect of the present invention, a device for manipulation of a syringe needle and sharps disposal is provided in combination with a surgical drape having an adhesive surface on its underside, which enables the surgical drape to be secured to a suitable working surface and thus facilitates single-handed manipulation and sharps disposal. Beneficially, the device includes a hollow chamber for sharps disposal, a wall provided with at least one aperture adapted for capping and uncapping a syringe needle, and a base with an adhesive surface. Advantageously, the surgical drape includes a marked area on its topside indicating appropriate positioning of the device on the surgical drape, and the adhesive surface on its underside results in the device being generally immovable after the surgical drape is adhered to a suitable working surface and the device is positioned on and adhered to the surgical drape.

In accordance with another aspect of the invention, a device for manipulation of a syringe needle and sharps disposal includes an end wall provided with one or more of the previously described aperture, and the end wall includes advantageous features for guiding a needle tip into a needle cap, when using one-hand. Accordingly, the end wall beneficially includes at least one flange-like portion and is provided with a peripheral rim which extends from the end wall so that the aperture is within a space defined by the rim. In this aspect of the invention, the device includes a hollow chamber for sharps disposal, and an opening to the hollow chamber is in a wall disposed generally perpendicular to the end wall.

In accordance with yet another aspect of the invention, a device for manipulation of a syringe needle and sharps disposal includes a hollow chamber for sharps disposal and is provided with a cover including a leg portion adapted to frictionally engage an opening to the hollow chamber. In addition, the device includes an end wall provided with one or more of the previously described aperture, and the cover advantageously includes an end portion adapted to cover the aperture. Beneficially, the cover further includes a top portion from which the leg portion depends and to which the end portion is joined, and the top portion has a horizontal extent such that when the leg portion is frictionally engaged in the opening, the top portion extends beyond the end wall and the end portion is spaced from the end wall a distance sufficient to accommodate a needle cap in the aperture.

In yet a further aspect of the invention, a device for manipulation of a syringe needle and sharps disposal includes an end wall provided with at least one aperture adapted for capping and uncapping a syringe needle, and the aperture tapers inwardly, and the end wall structure defining the aperture is a harder material than a polypropylene needle cap such that when a polypropylene needle cap is engaged in the inwardly tapered aperture, the aperture cuts into the needle cap. In this aspect, the device includes a hollow chamber for sharps disposal.

Additional advantages and beneficial features of the present invention are set forth in the drawing and detailed description, and in part will become apparent to those skilled in the art upon examination of the drawing and detailed description or may be learned by practice of the invention. In the drawing and detailed description, there is shown and essentially described only a preferred embodiment of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

FIG. 1 is a perspective view of a preferred device in accordance with the present invention;

FIG. 2 is a partially exploded view of the device of FIG. 1;

FIG. 3 is a cross-sectional view taken substantially along line 3—3 of FIG. 2, of the receptacle;

FIG. 4 is an enlarged cross-sectional view taken substantially along line 4—4 of FIG. 1;

FIG. 5 is a perspective view of the receptacle of FIG. 2 fixed on a sterile field during use;

FIG. 6 is a cross-sectional view taken substantially along line 6—6 of FIG. 5, showing the receptacle and sterile field fixed on a working surface, and showing the cover in phantom and needles in the needle sheaths;

FIG. 7 is a cross-sectional view taken substantially along line 7—7 of FIG. 5, but otherwise similar in content to FIG. 6;

DETAILED DESCRIPTION OF THE INVENTION

Figure 8:
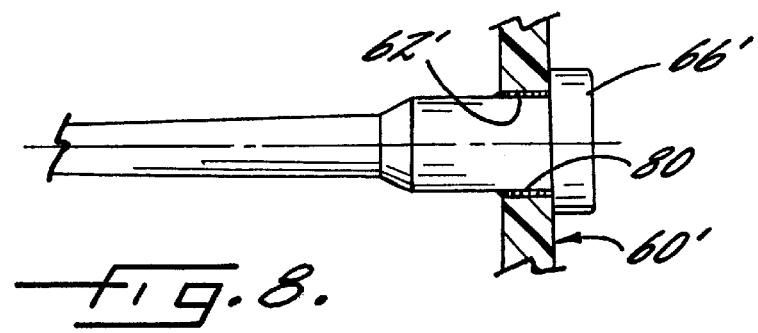
FIG. 8 is an enlarged cross-sectional view like FIG. 4 of an aperture/needle cap variation.

In accordance with one aspect of the present invention, a device for manipulation of syringe needles and sharps disposal may be immovably fixed on a sterile field, and a user may keep one hand free while using the device. In accordance with another aspect of the invention, a device for manipulation of syringe needles and sharps disposal includes advantageous features for guiding a needle tip into a needle cap, when one hand is used. In accordance with yet another aspect of the invention, a device for manipulation of syringe needles and sharps disposal includes a protective cover which prevents accidental loss of used sharps from the device. In accordance with a further aspect, a device for manipulation of syringe needles and sharps disposal includes an aperture for capping and uncapping a needle, which secures a needle cap by cutting into the needle cap.

Furthermore, by the present invention, needles may be kept organized, and needles with or without caps, and other sharps may be kept from being loose during surgery. As will be understood, terms such as "top", "upper", "under", "horizontal", "vertical" and the like are relative, and have been particularly used in the description with reference to the drawing to assist understanding.

Referring to FIGS. 1 to 3, a preferred device 10 in accordance with the present invention, beneficially includes a disposable receptacle 12 and a cover 14 made from a sterilizable, medical grade material. The receptacle conveniently has a barn-like shape with a top wall 16, opposing angular side walls 18, 20 and a base 22 injection molded from a suitable plastic material. The material should be incineratable or recyclable. Advantageously, device 10 is of a size which fits in a typical medical or dental procedure tray, although in use the device will typically be adhered to a suitable working surface outside a procedure tray.

With reference to FIG. 3 in particular, base 22 is advantageously provided on a lower surface with an adhesive layer 24 conveniently covered by a removable protective layer 26 of non-stick material. To this end, the base may be made adhesive by use of a double-sided adhesive foam pad of about the same dimensions as the base, or coated with an adhesive, or the like. In any event, the adhesive surface advantageously enables receptacle 12 to be securely positioned for use.

Figure 9:
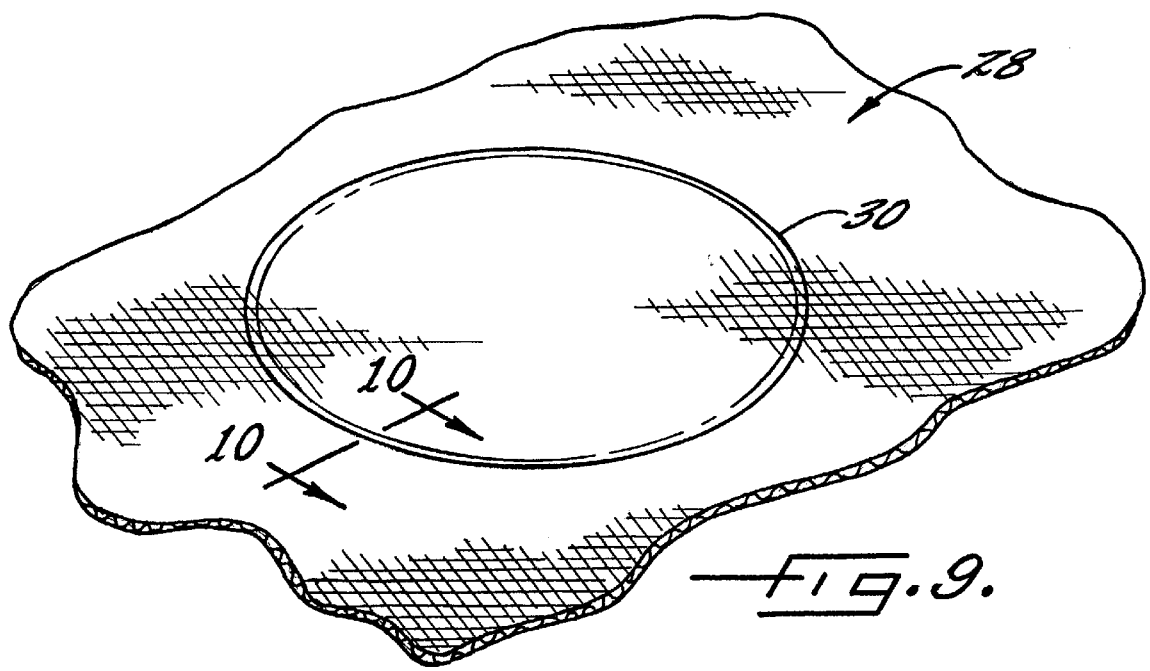
FIG. 9 is a perspective view of the topside of a surgical field/drape beneficially used in combination with a device in accordance with the present invention.
Figure 10:
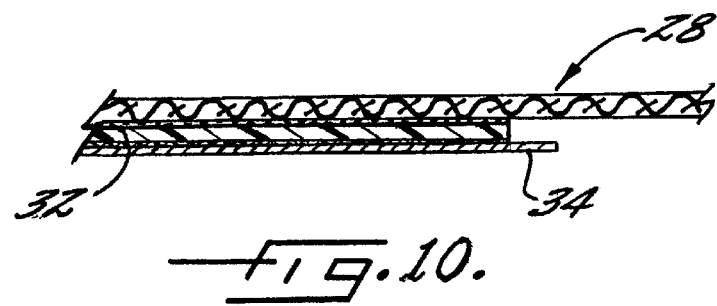
FIG. 10 is a partial cross-sectional view of the surgical field/drape of FIG. 9.

With reference also to FIGS. 9 and 10, device 10 is beneficially provided in a sterile wrap or surgical field/drape 28 having a marked area 30 on an upper surface to indicate appropriate positioning of base 22 on drape 28, and having on a portion of its underside disposed generally beneath the marked area so as to secure the drape to a suitable working surface and make the device generally immovable in use, an adhesive area 32 conveniently covered by a peel-away protective layer 34 of non-stick material. In the case of suitable adhesives, either or both protective layers would not be necessary; a pressure-sensitive adhesive is typically a convenient adhesive.

Referring again particularly to FIGS. 2 and 3, receptacle 12 includes conveniently in top wall 16, an opening 40 in the form of an elongated slot which leads to a hollow chamber 42 beneficially sized to hold a plurality of suture needles S (shown in FIGS. 6 and 7). Slot 40 includes a gap G, and suitably communicates with a restriction passageway 44 which terminates in a tapered upper portion 46 of the hollow chamber. The upper portion is generally frustum shaped when viewed in cross-section, and becomes larger away from slot 40. Opposing interior walls 48, 50 are angular and define the restriction passageway and upper portion 46. Also defining hollow chamber 42 are an inside surface 52 of base 22, and interior walls 54, 56 which intersect and abut walls 48, 50, respectively. Desirably, interior walls 54, 56 intersect side walls 18, 20, respectively.

With reference to FIGS. 2 to 4 particularly, receptacle 12 advantageously further includes a flange-like end wall 60 provided with apertures 62, 64 of a suitable size and configuration for engaging needle sheaths or caps 66. Apertures 62 lead to an interior chamber 72 for receiving the portion of a needle cap which extends inwardly of end wall 60, whereas apertures 64 lead to an interior chamber 74. Conveniently, an opposite end wall 70 of receptacle 12 limits the depth of chambers 72, 74; but in any event, the depth is sufficient to accommodate the length of typical capped surgical needles.

Beneficially as best illustrated in FIGS. 2 and 4, apertures 62, 64 are defined by numerous faces 76, and end wall 60 has a suitable cross-sectional width for providing engagement with a needle cap. Referring particularly to FIGS. 4 and 5, shown engaged in upper aperture 62 is a typical elongated, tapered needle cap having spaced peripheral ridges 78, which assist in securing the needle cap within the aperture for use of receptacle 12, as for instance illustrated by FIG. 5, to remove a needle N from a syringe and re-sheath the needle. Other aperture configurations may be used, provided that the hold of the aperture on a given needle cap provides for single-handed use of the receptacle. If desired, the apertures may vary in size from one another to accommodate needle caps of varying cross-sectional diameter.

Preferably, apertures 62 taper inwardly (best seen in FIG. 4), and the end wall structure defining the apertures is a harder material than a polypropylene needle cap such that when a polypropylene needle cap is engaged in the inwardly tapered aperture, the aperture cuts into the needle cap. To achieve this result, the end wall may be made from a suitable plastic material such as polystyrene.

Alternatively, as illustrated for a smooth bore aperture 62' in FIG. 8, the receptacle may include one or more needle caps 66' integral with, and extending axially through, the apertures. In this case, needle caps may be conveniently fixed or fused to the apertures in a conventional way such as by use of a suitable adhesive 80.

Referring to FIGS. 2 and 3 and also to FIGS. 5 to 7, interior walls 48, 54 bridge between end walls 60, 70 and separate chamber 72 from hollow chamber 42. Similarly, interior walls 50, 56 bridge between end walls 60, 70 and separate chamber 74 from hollow chamber 42. Desirably, hollow chamber 42 is thus isolated from needle cap chambers 72, 74.

Conveniently, top wall 16, side walls 18, 20, base 22, end wall 70, and the interior walls are injection molded as a unit, and end wall 60 is made separately and glued on. If desired, polystyrene can be used for the receptacle and for the cover. Conveniently, end walls 60, 70 are generally perpendicularly disposed relative to top wall 16.

Referring particularly to FIGS. 2 and 6, to enclose suture needles S disposed of within hollow chamber 42, cover 14 (shown in phantom in FIG. 6) advantageously includes a leg portion 82 of a thickness adapted to frictionally engage gap G of the slot. Suitably, as can be seen from FIG. 6, restriction passageway 44 has a gap which is about the same as that of the slot, and leg portion 82 has a vertical extent that exceeds the thickness of top wall 16 and frictionally engages the restriction passageway. Beneficially, the cover should not be easily removable from the receptacle after engagement with the receptacle; thus, it may not be desirable to provide the device with the cover engaged.

Advantageously, with reference particularly to FIGS. 5 and 6, end wall 60 includes flange-like portions 84 which extend outwardly beyond side walls 18, 20, and a peripheral rim 86. Rim 86 extends around and forms the peripheral edge of the end wall, and also beneficially extends from the end wall and is continuous so that the apertures are within a space defined by the rim. The flange-like portions and rim serve to guide a needle tip into a needle cap when receptacle 12 is used as illustrated in FIG. 5.

Referring particularly to FIGS. 2 and 4 to 7, to cover caps and needles in apertures in end wall 60, cover 14 (shown in phantom in FIGS. 6 and 7) beneficially includes an end portion 88 of a size and shape suitable for covering the apertures, and which is spaced from end wall 60 a sufficient distance to accommodate caps and needles in the apertures. Conveniently, to this end and provide structural support for end portion 88, leg portion 82 has a horizontal extent (best seen in FIGS. 4 and 7) that exceeds the width of slot 40 and extends a distance sufficient to space the end portion away from end wall 60, a top portion 90 of peripheral rim 86 and end wall 60 are provided with a notch 92 which communicates with slot 40 and restriction passageway 44, and an end 94 of leg portion 82 extends through the notch and exterior to receptacle 12, to intersect with, and be joined to, end portion 88, which is generally perpendicular to leg portion 82.

To provide additional structural support for end portion 88, cover 14 is suitably provided with a top portion 96 from which leg portion 82 depends and which is coextensive with leg portion 82 so as likewise to intersect with, and be joined to, end portion 88. Conveniently, to this end, as clearly shown in FIG. 4, top portion 90 of the peripheral rim may be co-planar with receptacle top wall 16, and top portion 96 of cover 14 may be planar from end to end.

In use, device 10 is beneficially provided in a sterile wrap 28, which is opened, and protective layer 34 is peeled away from adhesive area 32 on the underside of surgical drape 28 and the surgical drape is secured to a working surface W. Thereafter, receptacle 12 is positioned on the surgical drape and approximately centered over marked area 30 on the topside of the surgical drape, and the base of receptacle 12 is adhesively secured to the surgical drape. As a result, receptacle 12 may advantageously be immovably fixed on a sterile field for use.

Cover 14 is conveniently placed on the sterile field away from receptacle 12. During surgery, used suture needles may be dropped through opening 40 into hollow chamber 42. A needle can be mounted to a syringe and removed from a needle cap engaged in, or integral with, a suitable aperture, by pushing the needle-gripping end of a syringe into the boss portion of the needle, rotating the syringe and withdrawing the syringe and needle as a unit. Similarly, and with reference to FIG. 5, a needle N can be removed from a syringe and re-sheathed by inserting the needle into a needle cap engaged in, or integral with, a suitable aperture until the needle boss engages with the inner sheath wall and thereafter rotating the syringe in an opposite direction from that used to mount the needle on the syringe, and withdrawing the syringe.

As can be understood, the foregoing sequence could be reversed, and a device in accordance with the present invention, has many applications. For instance, a needle cap in receptacle 12 may be used as a storage place for a used needle with a view to re-using the needle when permitted. Thus, needles may be safely kept, ready for use, and be retrieved from a specific location.

In any event, with reference to FIGS. 6 and 7, when receptacle 12 has been used, cover 14 (shown in phantom) is engaged with receptacle 12 by pushing the cover leg portion into opening 40. In this way, by a single act, the user closes chamber 42, blocks access to sheathed needles, and prevents sheathed needles from accidentally falling out of the receptacle.

Having described the invention by reference to a preferred embodiment thereof, it will be apparent that modifications and variations are possible without departing from the scope of the invention defined in the appended claims. Thus, while particular shapes have been shown for the receptacle and the chamber for sharps disposal, it will be appreciated that other shapes can be used as well. Furthermore, while polystyrene has been disclosed as a suitable material, other suitable sterilizable, medical grade materials can be used. Moreover, while four apertures have been shown, it will be appreciated that fewer apertures or more apertures may be used.

What is claimed is:

1. A device for manipulation of a syringe needle and for receiving sharps comprising a hollow chamber for receiving sharps, a wall provided with at least one aperture adapted for capping and uncapping a syringe needle, and a base comprising a first adhesive surface, in combination with a surgical drape comprising on its underside a second adhesive surface.

2. The device of claim 1, wherein said surgical drape comprises a marked area on its topside indicating appropriate positioning of said device on said surgical drape, and said second adhesive surface is disposed on a portion of the surgical drape underside in a location rendering the device generally immovable in use after adhesion to a working surface.

3. The device of claim 1, wherein said first adhesive surface is covered by a removable layer of non-stick material, and said second adhesive surface is likewise covered by a removable layer of non-stick material.

4. The device of claim 1, wherein said at least one aperture has a suitable size and configuration for engaging a needle cap sufficiently for single-handedly capping and uncapping a syringe needle.

5. The device of claim 1, further comprising a needle cap integral with, and extending through, said at least one aperture.

6. A device for manipulation of a syringe needle and for receiving sharps comprising a hollow chamber for receiving sharps and an opening to said hollow chamber, and an end wall provided with at least one aperture adapted for capping and uncapping a syringe needle, wherein said end wall comprises at least one flange portion and is provided with a peripheral rim which extends from said end wall so that said at least one aperture is within a space defined by said rim, and wherein said opening is in a wall disposed generally perpendicular to said end wall.

7. The device of claim 6, wherein said at least one aperture leads to a second hollow chamber, and an interior wall separates said hollow chamber for receiving sharps from said second hollow chamber.

8. The device of claim 6, wherein said hollow for receiving sharps comprises a tapered upper portion having a generally frustrum shaped cross-section.

9. The device of claim 6, wherein said at least one aperture has a suitable size and configuration for engaging a needle cap sufficiently for single-handedly capping and uncapping a syringe needle.

10. The device of claim 6, further comprising a needle cap integral with, and extending through, said at least one aperture.

11. A device for manipulation of a syringe needle and for receiving sharps comprising a hollow chamber for receiving sharps, an opening to said hollow chamber, an end wall provided with at least one aperture adapted for capping and uncapping a syringe needle, and a cover comprising a leg portion adapted to frictionally engage said opening and an end portion adapted to cover said at least one aperture.

12. The device of claim 11, wherein said cover comprises a top portion from which said leg portion depends and to which said end portion is joined, and said top portion has a horizontal extent such that when said leg portion is engaged in said opening, said top portion extends beyond said end wall and said end portion is spaced from said end wall a distance sufficient to accommodate a needle cap in said at least one aperture.

13. The device of claim 11, wherein said opening has a certain gap and communicates with a restriction passageway having a gap which is about the same as that of said opening, and said leg portion has a vertical extent which frictionally engages said restriction passageway when said leg portion is engaged in said opening.

14. The device of claim 11, wherein said opening is an elongated slot, and said end wall is provided with a notch, and said leg portion has a horizontal extent such that when said leg portion is engaged in said elongated slot, an end of said leg portion extends through said notch and beyond said end wall and is joined to said end portion.

15. The device of claim 11, wherein said opening is in a wall disposed generally perpendicular to said end wall, and said leg portion is generally perpendicularly disposed relative to said end portion.

16. The device of claim 11, wherein said at least one aperture has a suitable size and configuration for engaging a needle cap sufficiently for single-handedly capping and uncapping a syringe needle.

17. The device of claim 11, further comprising a needle cap integral with, and extending through, said at least one aperture.

18. A device for manipulation of a syringe needle and for receiving sharps comprising a hollow chamber for receiving sharps, an opening to said hollow chamber, and an end wall provided with at least one aperture adapted for capping and uncapping a syringe needle, wherein said at least one aperture tapers inwardly, and the end wall structure defining said at least one aperture is of sufficient cross-section and is a harder material than a polypropylene needle cap such that when a polypropylene needle cap is engaged in the at least one inwardly tapered aperture, said end wall remains rigid and said aperture cuts into the needle cap.

19. The device of claim 18, wherein said at least one aperture comprises a plurality of faces.

20. A device facilitating engagement and disengagement between a syringe needle and a syringe, the device comprising:

a base, an end wall upstanding from said base and provided with an aperture therethrough, a cap for a syringe needle fixedly mounted in said aperture, and walls enclosing said cap, one of said walls enclosing said cap comprising an opening therein; and a cover having a first portion configured to frictionally engage said opening in said one of said walls and a second portion that prevents access to said cap when said first portion is frictionally engaged in said opening.

* * * * *